(12) United States Patent
Brockwell (10) Patent No.: US 8,869,592 B2
(45) Date of Patent: Oct. 28, 2014

(54) TWO STAGE THERMAL MODULATOR FOR GAS CHROMATOGRAPHY WITH THERMALLY MATCHED GROUNDING POINT

(75) Inventor: Timothy G. Brockwell, Boerne, TX (US)

(73) Assignee: Southwest Research Institute, San Antonio, TX (US)

( * ) Notice: Subject to any disclaimer, the term of this patent is extended or adjusted under 35 U.S.C. 154(b) by 285 days.

(21) Appl. No.: 13/358,030

(22) Filed: Jan. 25, 2012

(65) Prior Publication Data
US 2013/0186175 A1 Jul. 25, 2013

(51) Int. Cl.
*G01N 30/46* (2006.01)

(52) U.S. Cl.
USPC .......................................... 73/23.39; 73/23.42

(58) Field of Classification Search
CPC .......................... G01N 30/465; G01N 30/6039
See application file for complete search history.

(56) References Cited

U.S. PATENT DOCUMENTS

| | | | | |
|---|---|---|---|---|
| 4,735,259 | A | * | 4/1988 | Vincent ........................... 165/47 |
| 5,135,549 | A | | 8/1992 | Phillips et al. |
| 7,284,409 | B2 | | 10/2007 | Hasselbrink et al. |
| 7,293,449 | B2 | | 11/2007 | Hasselbrink et al. |
| 2005/0268693 | A1 | | 12/2005 | Hasselbrink et al. |

OTHER PUBLICATIONS

Cavagnino, "An Introduction and Overview on Comprehensive Two-Dimensional Gas Chromatography (GCxGC): New Opportunities for Unresolved Complex Mixtures," 5th Thermo Scientific High Resolution GC/MS Meeting on POPs, Barcelona, Apr. 29-30, 2010 (34 pages).

Libardoni, et al., "At-column heating and a resistively heated, liquid-cooled thermal modulator for a low-resource bench-top GC6GC," J. Sep. Sci. 2006, 29, 1001-1008.

Kim et al., "A low power, high-speed miniaturized thermal modulator for comprehensive 2D gas chromatography," 2010 IEEE 23rd International Conference on Micro Electro Mechanical Systems (MEMS), Jan. 24-28, 2010, pp. 124-127.

Scherer, "Comprehensive Two-Dimensional Gas Chromatography coupled with Time-of-Flight Mass Spectrometry for Broad Spectrum Organic Analysis GCxGC-TOFMS," GACID Harsh Environment Mass Spectrometry workshop Sep. 22, 2003 Sarasota, FL, 31 pages.

* cited by examiner

*Primary Examiner* — Paul West
(74) *Attorney, Agent, or Firm* — Grossman, Tucker et al.

(57) ABSTRACT

Disclosed herein are two stage thermal modulators that are useful in the separation of the components of an analyte sample in an analytical method, such as gas chromatography. In some embodiments, the thermal modulators described herein include a modulator column coupled to at least one ground point so as to define a plurality of stages that may be independently temperature modulated. In some cases, the modulator column (or stages thereof adjacent to a ground point) and the ground point are thermally matched, so as to limit or eliminate the formation of a temperature differential between the modulator column and a ground point.

23 Claims, 9 Drawing Sheets

TWO STAGE THERMAL MODULATOR FOR GAS CHROMATOGRAPHY WITH THERMALLY MATCHED GROUNDING POINT

STATEMENT OF GOVERNMENT INTEREST

This invention was made with government support under government grant number CHE-0650647, awarded by the National Science Foundation. The government has certain rights in the invention.

BACKGROUND

Gas chromatography (hereafter, "GC") is a widely used method for the analysis of chemical compounds. It is used in a large number of applications, including but not limited to forensics, exhaust gas monitoring, environmental analysis, and industrial process monitoring.

In GC, a sample of analyte vapor (hereafter, "analyte") is introduced, typically with a carrier gas, into a small capillary or column. The interior diameter of the column is coated with a thin film, known as a "stationary phase." The various components of the analyte have different affinities for the stationary phase and the carrier gas. As a result of the flow of carrier gas through the column, the components of the analyte move through the column at different average rates and (ideally) separate from one another. As they exit the column, the separated components of the analyte can be detected with a number of different detectors, such as a flame ionization detector and/or a mass spectrometer. Because the analyte is exposed to a column containing a single stationary phase, this type of GC is often referred to as one-dimensional GC (hereafter, "1D GC").

When an analyte contains a number of compounds that have similar affinity to a stationary phase, separation of those compounds using 1D GC may be difficult or impossible. To address this issue, two dimensional (2D) GC, or GC×GC systems have been developed. In general, 2D GC systems include two chromatography columns that are coupled in series. The interior diameter of each column is coated with a different stationary phase. In this way, compounds having similar affinity (e.g., boiling point and/or polarity) for the stationary phase of the first column may be separated due to their differing affinity (orthogonality) for the stationary phase of the second column. As a result, compounds that would normally co-elute in a 1D GC system can be separated using 2D GC.

Although 2D GC can enable the separation of a wide variety of compounds, it is possible that bands of analyte compounds separated in the first column may co-elute with bands of analyte compounds separated in the second column. As a result, errors may be introduced into the analysis of the sample. To address this issue, devices for trapping and accumulating analyte from the first column of the 2D GC while conducting analysis in the second column of the 2D GC have been proposed. In particular, devices known as thermal modulators have been placed between the first column and the second column.

Figure 1:
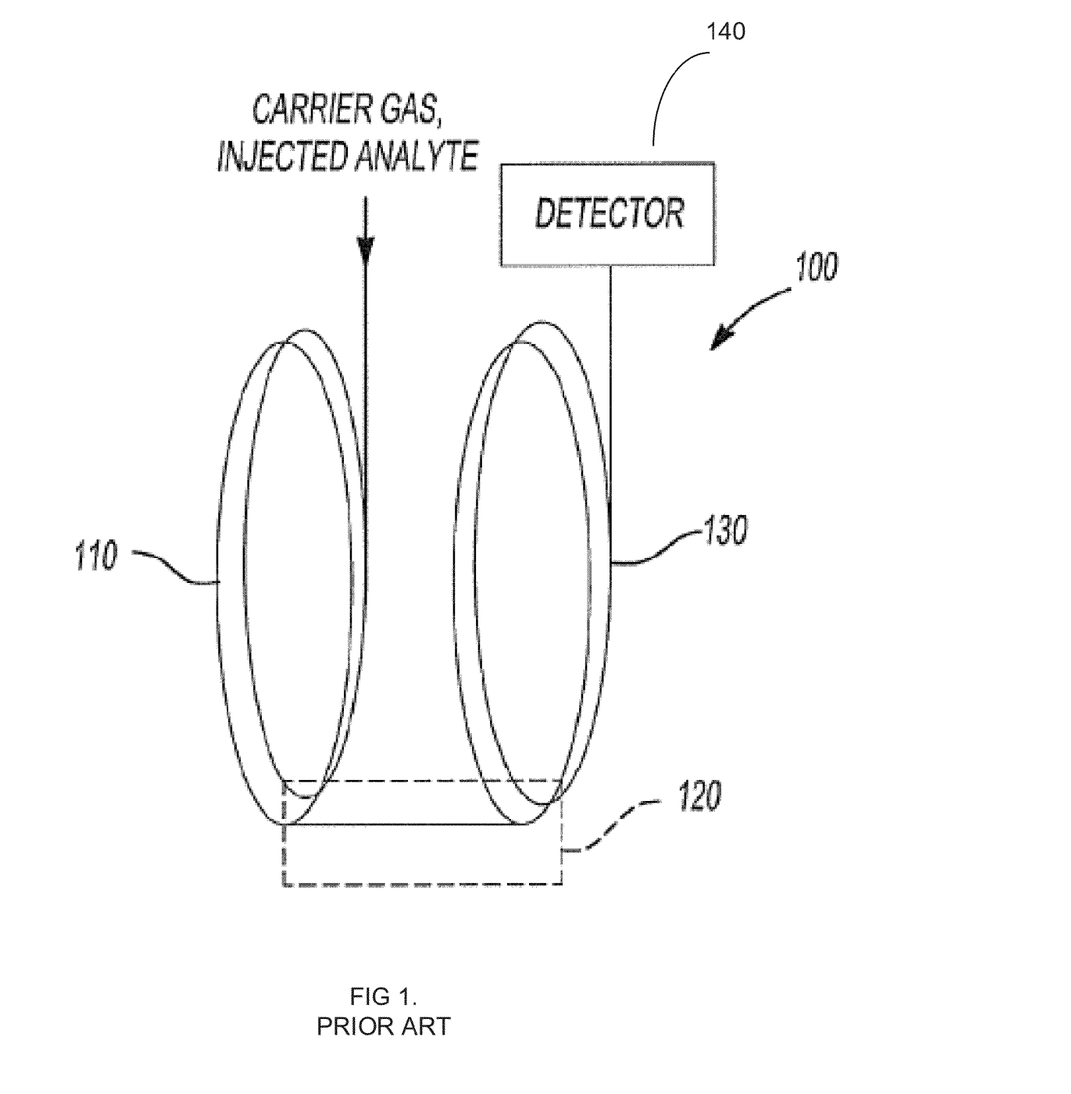
FIG. 1 illustrates the basic construction of a two dimensional gas chromatography system according to the prior art.

A basic diagram outlining the construction of a 2D GC incorporating a thermal modulator is shown in FIG. 1. As shown, 2D GC 100 includes first column 110 including a first stationary phase, and second column 130 including a second stationary phase. First column 110 and second column 130 are coupled in series by thermal modulator 120. Carrier gas and analyte are injected into first column 110, and separated components of the analyte exit second column 130. Upon exiting second column 130, the separated compounds enter the inlet of a detector 140.

Thermal modulator 120 includes a short segment of capillary, hereafter referred to as a "modulator column." The modulator column is rapidly cooled so as to trap the analyte leaving first column 110 within the modulator column. For example, the modulator column may be cooled to −40° C. for 1-10 seconds to accumulate (trap) analyte peaks from the first column. The modulator column may then be rapidly heated to a high temperature (e.g., 100-300° C.) to vaporize the trapped analyte and release it to second column 130. By repeatedly cycling (i.e., thermally modulating) the modulator column from between a low temperature and a high temperature, "pulses" of analyte from first column 110 are eluted into second column 130. Because only a single section of the modulator column is modulated, modulator 120 is referred to herein as a "single stage thermal modulator."

Put in other terms, thermal modulator 120 acts as an alternating trap and injector. That is, thermal modulator 120 continually traps, focuses, and re-injects analyte at a user defined time constant throughout the analysis of a sample, as described below. Because thermal modulator 120 focuses the analyte peaks in a modulator column, a 2D GC system can exhibit improved signal to noise relative to 1D GC system. As a result, 2D GC instruments often can detect smaller quantities of components within an analyte than 1D GC instruments, in addition to providing the separation benefits noted above.

Figure 2A:
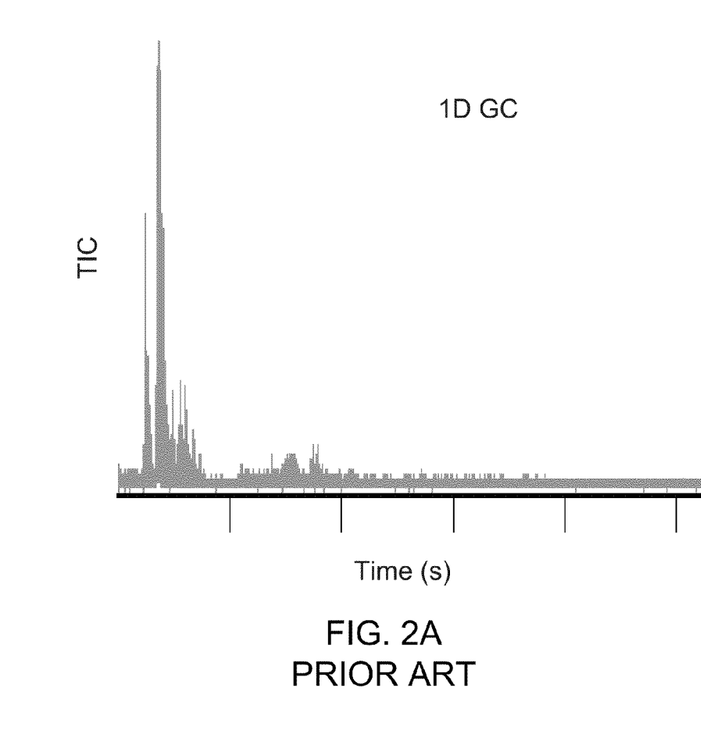
FIGS. 2A and 2B are plots of the analysis of an identical sample using prior art 1D GC and 2D GC, respectively.
Figure 2B:
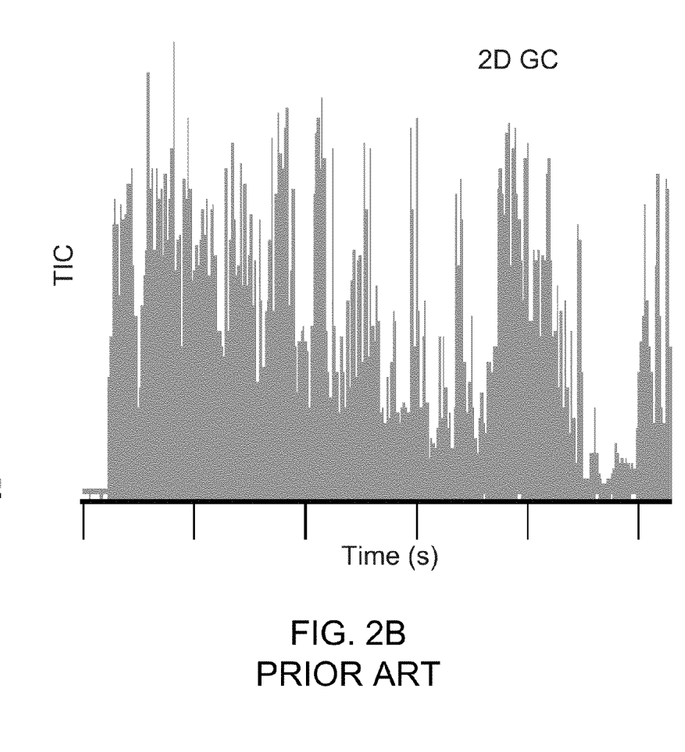

To illustrate the performance of 2D GC, relative to 1D GC, reference is made to FIGS. 2A and 2B, which plot the results of an analysis of the same sample by 1D GC (FIG. 2A) and 2D GC (FIG. 2B). As shown, significantly more peaks can be identified using 2D GC (FIG. 2B) than 1D GC (FIG. 2A).

In order to achieve desirably narrow second dimension peak widths, many commercial 2D GC instruments employ a cryogenic cooling system. In such systems, cold focusing in the modulator is achieved by rapidly cooling and warming the modulator column, as described above. Rapid cooling may be achieved, for example, by intermittently directing liquid nitrogen (LN2), a cooled gas, or liquid carbon dioxide onto the modulator column. In contrast, rapid heating may be accomplished with a hot gas (e.g. nitrogen) jet. Although cooling and heating a modulator column in this manner is effective, it requires the use of a large quantity of costly consumables. Moreover, it limits the use of many 2D GC systems to the laboratory. As such, many 2D GC systems cannot be employed as a portable instrument.

Investigation has been made into the development of a liquid cooled, single stage thermal modulator in which the modulator column is cooled by a cold "finger" and an immersion cooler. While this technique eliminates the use of cryogens, the size of the cold finger and immersion cooler still limit the portability of the instrument.

In addition to portability limitations, many 2D GC instruments utilize single stage modulators, such as described above. In these instruments, the minimum peak width that the single stage thermal modulator can transfer to the second column may be limited. To permit the delivery of even narrower (i.e., more focused) peaks to the second column, two stage thermal modulators have been proposed. Generally, a two stage thermal modulator operates by independently heating and cooling two sections (stages) of a single modulator column. This technique allows peaks from the first column to be focused more tightly in the second stage of the modulator column, prior to transfer to the second column of the 2D GC. As a result, two stage modulators can produce narrower and higher peaks, resulting in both improved separation and improved sensitivity, relative to 1D GC or 2D GC systems employing a single stage thermal modulator.

Like single stage modulators, investigation has been made into two stage thermal modulators that are liquid cooled. While such systems have shown some promise, their performance is limited due to the size of the cooling system and the presence of a chilled region or "spot" between the two stages of the modulator column. This cold spot can hinder or even inhibit transfer of analyte peaks from the first stage to the second stage of the modulator, and potentially to the second column of the instrument. Even if analyte passes through the modulator to the second column, the cold spot can distort peak shape, or give rise to other artifacts, such as memory and bleed.

SUMMARY

One aspect of the present disclosure relates to two stage thermal modulators that are useful in the separation of components of an analyte sample, such as in a gas chromatography process. In non-limiting embodiments, the two stage thermal modulators include a housing having a cavity therein that is configured to contain a coolant. The two stage thermal modulators may further include a modulator column that is in thermal contact with the coolant, thereby defining a chilled region. In such non-limiting embodiments, a ground point is coupled to the modulator column within the chilled region and is operable to connect the modulator column to electrical ground. At least one power supply is coupled to a first point and a second point along the modulator column. The power supply operates to resistively heat a first stage of the modulator column and a second stage of the modulator column. The first stage is defined between the first point and the ground point, and the second stage is defined between the ground point and the second point.

In some embodiments, the modulator column and the ground point are thermally matched. In such non-limiting embodiments, the thermal modulators include a ground point having an electrical resistance, thermal mass, and CSA that are the same as the corresponding properties of adjacent stages of a modulator column, or which (individually or collectively) differ from the corresponding properties of such adjacent stages by an amount ranging from about −5% to about +5%, such as from about −1% to about +1%, or even about 0%.

Another aspect of the present disclosure relates to methods for temperature modulation in gas chromatography. In non-limiting embodiments of such methods, a sample is introduced into a modulator column of a two stage thermal modulator that is configured as described herein.

Yet another aspect of the present disclosure relates to modulator columns that are suitable for use in a two stage thermal modulator. In some embodiments, the modulator column includes a ground point, a first stage proximal to the ground point, and a second stage distal to the ground point. When an electric current is passed through the first stage and the grounding point or the second stage and the grounding point, the ground point exhibits a temperature that is less than about 5% different from the temperature of the first stage or the second stage, respectively.

BRIEF DESCRIPTION OF THE DRAWINGS

The accompanying drawings, which are incorporated in and constitute a part of this specification, illustrate several non-limiting embodiments of the present disclosure and, together with the description, serve to explain the principles of the present disclosure.

DESCRIPTION OF THE EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

In the context of multidimensional gas chromatography (GC), the terms, "column," "chromatography column" and "capillary" are used interchangeably herein to refer to the columns that interface with a thermal modulator.

As used herein, the term, "modulator column" means a column forming part of a thermal modulator, as described herein.

As used herein, the term "multidimensional gas chromatography" means a gas chromatography system or method in which at least two columns with different stationary phases are used.

As used herein the term, "stage" refers to a portion of a modulator column that may be heated and cooled independently of another portion of the modulator column. In some embodiments, and as will be described in detail below, the modulator columns described herein may be divided into multiple stages through the use of an electrical connection to ground, i.e., a ground point. For example, in embodiments wherein the modulator column may be resistively heated through the application of electric current, a ground point may be employed to divide the modulator column into two stages, i.e. a first stage between the ground point and a first point of contact of a power supply, and a second stage between the ground point and a second point of contact of a power supply.

As discussed in the background, thermal modulators having multiple stages have been developed, but their performance is limited for a variety of reasons. For example, conventional two stage thermal modulators often exhibit a temperature differential (e.g., a cold spot) at the interface between the first and second stages of the modulator column, e.g., at a ground point. This can result in peak broadening, measurement errors, and other problems, as noted above.

The inventors have discovered that the temperature differential issue in many conventional two stage modulators is attributable to the ground point used to define the first and second stage of the modulator column. Specifically, the inventors have discovered that the ground point in conventional two stage thermal modulators heats and cools at a different rate than the adjacent first and second stages of the modulator column. Although the modulator column and the ground point may be exposed to the same heating and cooling forces during modulation, differences in the mass and/or properties of the ground point and modulator column can result in the aforementioned temperature difference.

Accordingly, one aspect of the present disclosure relates to two stage thermal modulators that include at least one ground point that is thermally matched to adjacent stages of a modulator column, thereby reducing or eliminating the aforementioned temperature difference between adjacent stages of a modulator column.

As used herein, the term "thermally matched," when used in connection with a modulator column and a ground point, means that at least one characteristic that affects the heating of the ground point and adjacent stages of the modulator column differ from one another by about 5% or less. The phrase, "adjacent stages of a modulator column," refers to the portion of a modulator column that precedes or follows a ground point, respectively, and whose temperature may be independently set and or controlled.

Figure 3:
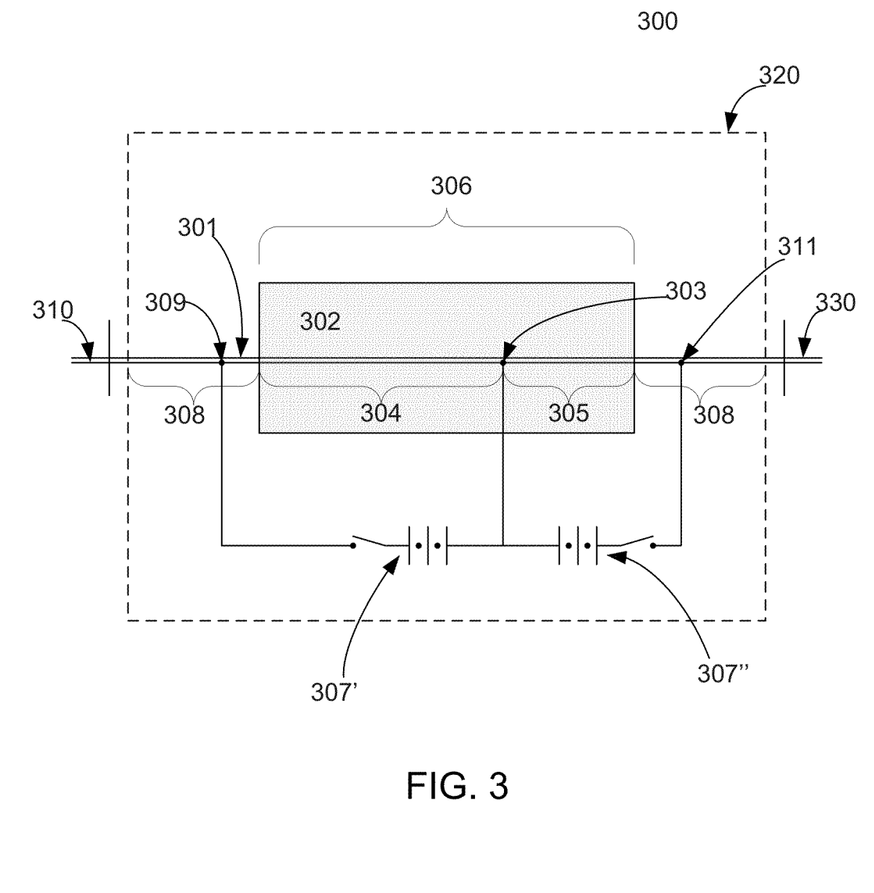
FIG. 3 is a simplified diagram of a non-limiting example of a two stage thermal modulator in accordance with the present disclosure, as used in a 2D GC.

To illustrate the concept of "adjacent stages of a modulator column," reference is made to FIG. 3. Generally, FIG. 3 illustrates the construction of non-limiting example of a 2D GC apparatus including a two stage thermal modulator in accordance with the present disclosure. As shown, 2D GC 300 includes first and second chromatography columns 310, 330, connected in series via two stage thermal modulator 320. More specifically, first and second chromatography columns 310 and 330 are connected to proximal and distal ends, respectively, of modulator column 301. Modulator column 301 (which may be resistively heated as described below) is coupled to ground point 303, which divides modulator column 301 into first (proximal) stage 304 and second (distal) stage 305. As shown, first stage 304 and second stage 305 are adjacent to ground point 303. Thus, first stage 304 and second stage 305 qualify as adjacent stages of a modulator column, relative to ground point 303.

In some embodiments, at least one characteristic that affects the heating of a ground point and the adjacent stages of a modulator column differ from one another by an amount ranging from about −5% to about +5%, such as about −1% to about +1%, or even about −0.5% to about +0.5%. In some embodiments, two or more (e.g., all) of the characteristics of the ground point and adjacent stages of the modulator column that affect the heating thereof differ by an amount ranging from about −5% to about +5%, such as about −1% to about +1%, or even about −0.5% to about +0.5%. And in some instances, one or more (e.g., all) of the properties affecting the heating of the ground point and adjacent stages of a modulator column are equal to one another.

The phrase, "characteristic that affects the heating of a ground point and adjacent stages of a modulator column," is used herein to refer to properties that impact the rate at which the temperature of a ground point and/or modulator column rises and falls in response to heating and cooling forces. Non-limiting examples of such properties include the mass, specific heat capacity, thermal mass (i.e., mass times specific heat capacity), and cross sectional area (CSA) of a ground point and adjacent modulator column stages. In instances where the modulator columns of the present disclosure are heated by the application of an electric current, electrical resistance is another characteristic affecting the heating of a ground point and adjacent stages of a modulator column.

Accordingly in some embodiments, the two stage thermal modulators described herein are configured such that at least one of the CSA, electrical resistance, mass, specific heat capacity, and thermal mass of a ground point differs from the corresponding property of adjacent stages of a modulator column by about 5% or less, about 1% or less, or even about 0.5% or less. In some cases, at least one of the CSA, electrical resistance, specific heat capacity, and thermal mass of a ground point is equal to the corresponding property of the adjacent stages of a modulator column.

By way of example, the two stage thermal modulators described herein may be configured such that the electrical resistance of a ground point equals the electrical resistance of surrounding modulator column stages, or differs from such stages by about 5% or less, about 1% or less, or even about 0.5% or less. Likewise, the two stage thermal modulators of the present disclosure may be configured such that the thermal mass of a ground point equals the thermal mass of surrounding modulator column stages, or differs from such stages by about 5% or less, about 1% or less, or even about 0.5% or less. Similarly, the two stage thermal modulators described herein may utilize a ground point having a CSA that equals the CSA of surrounding modulator column stages, or differs from such stages by about 5% or less, about 1% or less, or even about 0.5%.

The two stage thermal modulators described herein may also be configured such that two or more the aforementioned properties of a ground point and adjacent stages of a modulator column are the same, or differ from one another by about 5% or less, about 1% or less, or even about 0.5% or less. Thus for example, the two stage thermal modulators of the present disclosure may include a ground point having an electrical resistance and thermal mass that are the same as the corresponding properties of adjacent stages of a modulator column, or which (individually or collectively) differ from the corresponding properties of such adjacent stages by about 5% or less, about 1% or less, or about 0% or less. Likewise, the two stage thermal modulators of the present disclosure may include a ground point having an electrical resistance and CSA that are the same as the corresponding properties of adjacent stages of a modulator column, or which (individually or collectively) differ from the corresponding properties of such adjacent stages by about 5% or less, about 1% or less, or about 0% or less. And still further, the two stage thermal modulators of the present disclosure may include a ground point having an electrical resistance and specific heat capacity that are the same as the corresponding properties of adjacent stages of a modulator column, or which (individually or collectively) differ from the corresponding properties of such adjacent stages by about 5% or less, about 1% or less, or about 0% or less.

In some embodiments, the two stage thermal modulators described herein include a ground point having an electrical resistance and a thermal mass that are equal to the corresponding properties of adjacent stages of a modulator column. In other non-limiting embodiments, the two stage thermal modulators described herein include a ground point having a thermal mass and a CSA that are equal to the corresponding properties of adjacent stages of a modulator column.

The two stage thermal modulators described herein may also be configured such that all of the aforementioned properties of a ground point and adjacent stages of a modulator column are the same, or differ from one another by about 5% or less, about 1% or less, or about 0.5 or less. For example, the thermal modulators of the present disclosure may include a ground point having an electrical resistance, thermal mass, and CSA that are the same as the corresponding properties of adjacent stages of a modulator column, or which (individually or collectively) differ from the corresponding properties of such adjacent stages by about 5% or less, about 1% or less, or about 0% or less.

Put in other terms, the thermal modulators described herein may be configured such that a modulator column (or stages adjacent a ground point) has a resistivity R1, a thermal mass TM1, and a cross sectional area CSA1; and a ground point has a resistivity R2, a thermal mass TM2, and a cross sectional area CSA2, wherein one, two, or all of the following relationships is true:

R2 differs from R1 by less than or equal to about 5% (i.e., by an amount ranging from about −5% to about +5%);

TM2 differs from TM1 by less than or equal to about 5% (i.e., by an amount ranging from about −5% to about +5%); and CSA1 differs from CSA2 by less than or equal to about 5% (i.e., by an amount ranging from about −5% to about +5%).

In some embodiments, the thermal modulators described herein may be configured such that a modulator column (or stages adjacent a ground point) has a resistivity R1, a thermal mass TM1, and a cross sectional area CSA1; and a ground point has a resistivity R2, a thermal mass TM2, and a cross sectional area CSA2, wherein one, two, or all of the following relationships is true:

R2 differs from R1 by less than or equal to about 1% (i.e., by an amount ranging from about −1% to about +1%);

TM2 differs from TM1 by less than or equal to about 1% (i.e., by an amount ranging from about −1% to about +1%); and CSA1 differs from CSA2 by less than or equal to about 1% (i.e., by an amount ranging from about −1% to about +1%).

In further non-limiting embodiments, the thermal modulators described herein may be configured such that a modulator column (or stages adjacent a ground point) has a resistivity R1, a thermal mass TM1, and a cross sectional area CSA1; and a ground point has a resistivity R2, a thermal mass TM2, and a cross sectional area CSA2, wherein one, two, or all of the following relationships is true:

R2 differs from R1 by less than or equal to about 0.5% (i.e., by an amount ranging from about −0.5% to about +0.5%);

TM2 differs from TM1 by less than or equal to about 0.5% (i.e., by an amount ranging from about −0.5% to about +0.5%); and CSA1 differs from CSA2 by less than or equal to about 0.5% (i.e., by an amount ranging from about −0.5% to about +0.5%).

Finally, the thermal modulators described herein may be configured such that a modulator column (or stages adjacent a ground point) has a resistivity R1, a thermal mass TM1, and a cross sectional area CSA1; and a ground point has a resistivity R2, a thermal mass TM2, and a cross sectional area CSA2, wherein one, two, or all of the following relationships is true:

R2=R1;
TM2=TM2; and
CSA1=CSA2.

For the purpose of clarity and brevity, the present disclosure will now focus specifically on the construction and operation of an exemplary two stage thermal modulator in accordance with the present disclosure, wherein a single ground point is used to divide a modulator column into two stages.

Figure 4:
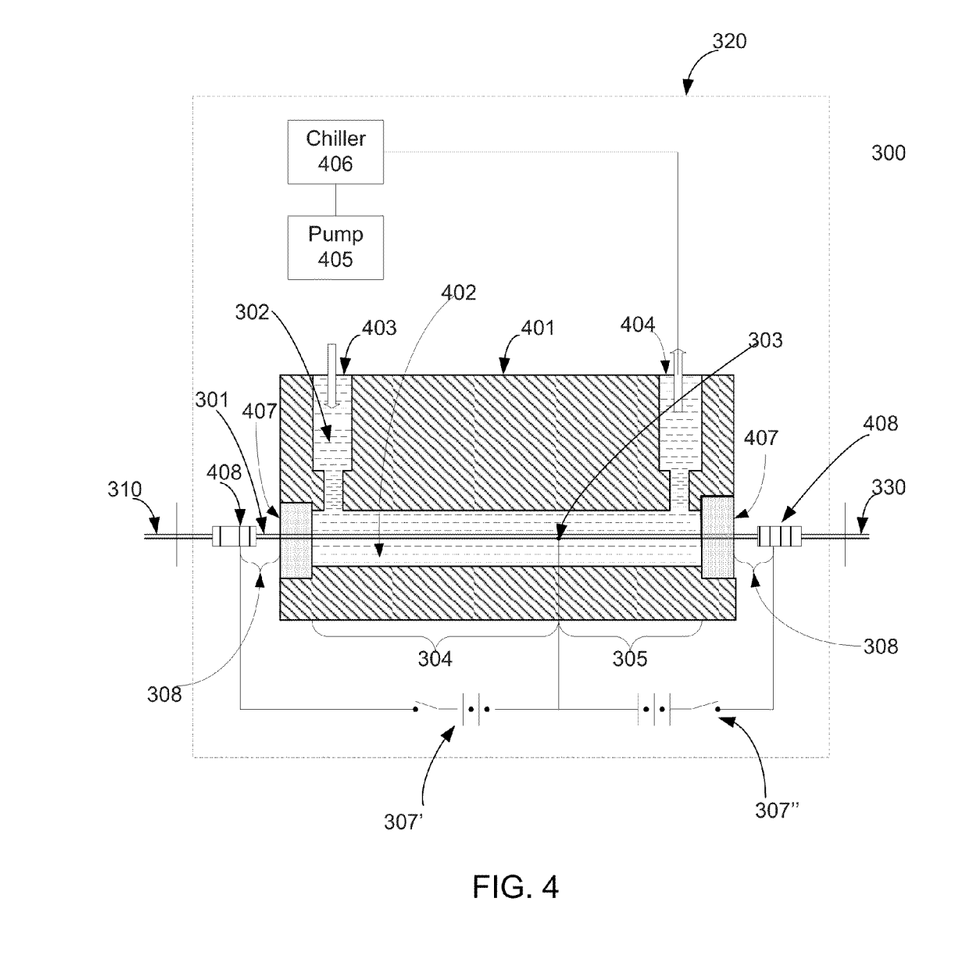
FIG. 4 is a cross sectional diagram of a non-limiting example of a two stage thermal modulator in accordance with the present disclosure, as used in a 2D GC.

Reference is therefore made to FIGS. 3 and 4, which illustrate non-limiting examples of a 2D GC including a two stage thermal modulator in accordance with the present disclosure. 2D GC 300 includes first and second chromatography columns 310, 330, coupled in series via modulator column 301 of two stage thermal modulator 320. At least a portion of modulator column 301 is in thermal contact with a coolant 302, thereby defining chilled region 306.

In the non-limiting examples shown in FIGS. 3 and 4, coolant 302 is a liquid coolant that surrounds a portion of modulator column 301 to define chilled region 306. Thus, FIGS. 3 and 4 depict a two stage thermal modulator 320 in which direct liquid immersion is used to cool a portion of modulator column 301, thereby defining chilled region 306.

While the present disclosure focuses on two stage thermal modulators that utilize a liquid coolant, other types of coolants may be used. For example, the systems and methods according to the present disclosure may utilize liquid, solid, and gaseous coolants, and combinations thereof.

With further reference to FIG. 3, first stage power supply 307' and second stage power supply 307" are generally configured to heat one or more portions of modulator column 301 by the application of electric current. First and second stage power supplies 307', 307" may be coupled to modulator column 301 at any suitable location for this purpose. In some embodiments, and as shown in FIG. 3, first stage power supply 307' is coupled to modulator column 301 at first point 309 proximal to chilled region 306 (i.e., closer to first chromatography column 310), and second stage power supply 307" is coupled to modulator column 301 at second point 311 distal to chilled region 306 (i.e., closer to second chromatography column 330).

Regardless of the location of first point 309 and second point 311, first stage power supply 307' and second stage power supply 307" are also coupled to ground point 303. Consistent with the foregoing discussion, ground point 303 is coupled to modulator column 301, and serves to provide a pathway to electrical ground. Ground point 303 may provide this connection directly or indirectly. In the former case, ground point 303 provides an uninterrupted connection between modulator column 301 and earth ground. In the latter case, ground point 303 may be coupled to another component of 2D-GC 300 or thermal modulator 320 that is connected (directly or indirectly) to earth ground. For example, in instances where two stage thermal modulator 320 includes a grounded housing, ground point 303 may be connected, e.g., via a set screw, a weld, or another suitable electrical connection, to the housing.

Ground point 303 may be coupled to modulator column 301 at any position along a length L of chilled region 306. In some embodiments, ground point 303 is coupled to modulator column 301 at a point that is greater or less than half way along the length L of chilled region 306. For example, ground point 303 may be coupled to modulator column at a point that is 10-40% of L, such as 15-20% of L, relative to an edge of chilled region 306. Thus, if chilled region 306 extends for 5 cm (L=5 cm), ground point 303 may be coupled to modulator column 301 at a point that is about 0.5 to about 2 cm (about 10-40% of L) away from an edge of chilled region 306. In a non-limiting embodiment, ground point 305 is located at a point that is about 20% of L, relative to an edge (e.g., a distal edge) of chilled region 306.

During the operation of dual stage thermal modulator 320, first stage and second stage power supplies 307' and 307" heat modulator column 301 by the application of electric current. Accordingly, and as will be discussed later, modulator column 301 may be at least partially formed from a material that has an electrical resistance suitable for heating in this manner. For example, the exterior wall of modulator column 301 may be formed at least in part by an electrically resistive material. Because modulator column 301 is not a perfect conductor (i.e., has an electrical resistance), power applied to modulator column 301 by power supplies 307' and 307" will be dissipated in the form of heat. Thus, upon application of electric current by power supply 307', first stage 304 of modulator column 301 may be warmed. Likewise, application of electric current by power supply 307" may warm second stage 305 of modulator column 301.

In this regard, it is noted that the resistance (R) of modulator column 301 (or first and second stages 304 and 305) may be defined mathematically using equation (1) below:

$$R = \rho L/A \quad (1)$$

Where R is the resistance of the modulator column in Ohms, ρ is the resistivity of the modulator column in ohm meters, L is the length of the modulator column in meters, and A is the area of the modulator column that is available to carry current in square meters. The resistivity ρ will vary with temperature, but for small variations around room temperature the change in ρ is approximately linear and may be described using equation (2) below:

$$\rho_T = \rho_0(1 + \alpha(T - T_0)) \quad (2)$$

where $\rho_T$ is the resistivity at temperature T, $\rho_0$ is the resistivity at room temperature, $T_0$ is room temperature in Kelvin, and T is the final temperature (also in Kelvin). α is the change in resistivity per unit temperature, and may derived using equation (3) below:

$$\Delta\rho/\rho_0 = \alpha\Delta T \quad (3)$$

where $\Delta\rho = \rho_T - \rho_0$ and $\Delta T = T - T_0$.

The energy used to heat the column may be determined by the voltage (V, Volts) and current (I, amps) applied to the modulator column, using the equation (4) below:

$$P = VI = V^2/R = I^2 R \quad (4)$$

where P is the power in watts (joules per second). If a constant voltage supply is assumed and temperature changes are neglected, substituting equation (1) into equation (4) yields equation (5) below:

$$P = I^2 A/\rho L. \quad (5)$$

The temperature rise in the column may be calculated using equation (6) below:

$$Q = c\Delta T m \quad (6)$$

where Q is the energy in joules, c is the specific heat capacity of the modulator column in joules per kilogram Kelvin (J/kg*K), ΔT is the temperature change in Kelvin, and m is the mass in kilograms of the material being heated. Combining equations (5) and (6) yields equation (7) below:

$$\Delta T = I^2 A t/\rho L c m \quad (7)$$

where t is the time in seconds that the current is applied to the modulator column. While this equation is simplistic and assumes that no heat is lost to the coolant, it is useful for the purpose of illustrating the impact of various properties on the heating of the modulator column and ground points in a two stage thermal modulator. It is also noted that the product of the specific heat capacity (c) and the mass (m) is referred to herein as "thermal mass."

As noted above, differences in temperature along modulator column 301 can lead to several analytical problems, including but not limited to peak broadening. To address this issue, the present disclosure contemplates two stage thermal modulators wherein one or more of the aforementioned variables are maintained at the point of contact between the ground point and the modulator column. That is, one or more of the aforementioned properties at or about the grounding point differ from corresponding properties of the modulator column by about 5% or less, about 2.5% or less, about 1% or less, or even about 0.5% or less. In some embodiments, one or more of the aforementioned properties at or about the grounding point is equal to the value of a corresponding property of the modulator column. For example, the value of m/L, ρ, c and A at or about the point of contact between the ground point and the modulator column may be maintained within the previously recited ranges.

In some embodiments, the ground point and modulator column are configured such they exhibit a substantially equivalent temperature in response to the same heating or cooling force. In this context, "substantially equivalent temperature" means that the temperature in the region of the grounding point is less than about 5% different from the temperature of the modulator column (e.g., the first and second stages) when both the modulator column and the grounding point are exposed to the same heating or cooling force. While the previous discussion describes one manner of accomplishing this goal, there are many mathematically possible combinations of m/l, ρ, c, A, CSA, etc. that will result in a desired change in temperature (ΔT). In practice, the selection of a material for the ground point will define the ρ, α and c, leaving m/L and A to be adjusted as design parameters.

With further reference to FIGS. 3 and 4, if chilled region 306 is considered alone (i.e., a single stage modulator that does not include a grounding point), A, ρ, and c are constant throughout the entire length of the modulator column. As a result, heating of the modulator column will be uniform along the entire length of the column, meaning that the rise in temperature will be the same at all points. In the context of a two stage modulator, however, ground point 303 is present between first stage 304 and second stage 305. As a result, current applied to the modulator column 301 will pass along the column and through the grounding point, thus increasing L. In addition, grounding point 303 increases the mass (m) that is being heated by the application of electric current. In practice, selection of the material for the ground point sets parameters ρ, α and c, leaving m/L and A as adjustable design parameters.

If the mass per unit length (m/L) along the current pathway increases at the grounding point, than the temperature rise in that region will be less than the temperature rise in first and second stages 304 and 305, respectively. As a result, a cold spot may occur at or near ground point 303. Similarly, if grounding point 303 is made of a material having a different resistivity (ρ) and/or specific heat capacity (c) than the modulator column, grounding point 303 may experience a higher or lower temperature rise in response to an applied electric current, relative to first and second stages 304 and 305. Moreover, if the α of grounding point 303 differs from the α of first and second stages 304 and 305, it may only be possible to match the temperature of grounding point 303 and modulator column 301 at a single point, which may limit the usefulness of the design. And finally, if the area (A) of ground point 303 differs from the area (A) of modulator column 301, then a different temperature rise may occur at grounding point 303 than at modulator column 301.

As noted above, first stage and second stage power supplies 307' and 307" may apply electric current to modulator column 301 at first point 309 and second point 311, respectively. Current applied at these points will return to ground (or the respective power supply) via ground point 303. As a result, first stage power supply 307' may heat first stage 304 of modulator column 301 independently of second stage 305. Likewise, second stage power supply 307" may heat second stage 305 of modulator column 301 independently of first stage 304. Of note is the fact that first stage 304 generally extends between ground point 303 and first point 309, i.e., in a direction proximal to ground point 303. Conversely, second stage 305 extends between ground point 303 and second point 311, i.e., in a direction distal to ground point 303.

FIG. 4 provides a more detailed illustration of a 2D GC apparatus 300 including a two stage thermal modulator 320 in accordance with the present disclosure. In addition to illustrating the components described above in connection with FIG. 3, FIG. 4 provides, among other things, additional detail with respect to an exemplary manner in which modulator column 301 may be cooled by a liquid coolant, e.g., coolant 302.

In the non-limiting example shown in FIG. 4, two-stage thermal modulator 320 includes a housing 401 with a cavity 402 formed therein. Housing 401 further includes inlet and outlet ports 403, 404. Coolant 302, which may be a moving liquid, flows into inlet port 403, through cavity 402, and out of outlet port 404. Upon exiting outlet port 404, coolant 302 may be redirected through the system (e.g., as in a closed loop), or discarded. The movement of coolant 302 may be facilitated by known means, such as by pump 405 or a hydrostatic pressure device.

Coolant 302 may be provided and/or maintained at a desirably low temperature by mechanical or other means. For example, and as shown in FIG. 4, coolant 302 may be provided or maintained at a desired temperature by chiller 406. Chiller 406 may operate to supply or cool coolant 302 at or to a desired temperature by any suitable means. For example, chiller 406 may be a mechanical device such as a thermoelectric cooler or a peltier cooler. In some embodiments, chiller 406 is a thermoelectric cooler, such as a two stage thermo-electric cooler.

While FIG. 4 depicts a non-limiting embodiment wherein coolant 302 is circulated by pump 405 and chilled by chiller 406, alternative methods of cooling modulator column 301 are possible. For example, the flow of coolant 302 through housing 401 is not required, and modulator column 301 may be cooled by immersion within a static coolant 302. In such embodiments, pump 405 would not be necessary and could be omitted. Moreover, modulator column 301 may be cooled by direct thermal contact with a cooled object, e.g., housing 401, a cold finger, etc., or by contact with a chilled gas stream.

As further shown in FIG. 4, Modulator column 301 may be supported by housing 401, and may be immersed in coolant 302 within cavity 402. As such, a chilled region may be established with cavity 402 of housing 401. Two stage thermal modulator 320 may further include septums 407, which may permit modulator column 301 to pass through cavity 402 of housing 401 without the leakage of coolant 302.

FIG. 4 also illustrates an exemplary connection of first stage and second stage power supplies 307', 307" to modulator column 301. As shown, first stage and second stage power supplies 307', 307" may be coupled to modulator column 301 via electrical connectors 408. Non-limiting examples of electrical connectors include clips, welds, solder connections and twist connections.

The systems and methods described herein may use a wide variety of coolants. As non-limiting examples of such coolants, mention is made of liquid coolants, solid coolants, gaseous coolants, and combinations thereof. Non-limiting examples of liquid coolants include liquefied gases, such as liquid nitrogen and liquid helium. Non-limiting examples of solid coolants include solidified gases such a solid carbon dioxide (i.e., dry ice), and metals/alloys that are mechanically or otherwise cooled to a desirably low temperature. Non-limiting examples of gaseous coolants include chilled gases such as chilled nitrogen and chilled carbon dioxide. In some embodiments, the coolant is liquid nitrogen.

As noted above, the modulator columns used in the present disclosure may be configured so as to include an exterior surface that is suitable for heating by the application of electric current. In such instances, the modulator columns described herein may have an exterior surface that is at least partially formed from conductive (but not perfectly conductive) materials, such as metals (including oxides, halides, borides, nitrides, and carbides thereof) alloys, carbon (e.g., graphite), composites, conductive polymers, and other materials. As non-limiting examples of materials that may be used to form at least a portion of the exterior of the modulator columns described herein, mention is made of: steel, stainless steel, and aluminum. In some embodiments, the modulator columns described herein are at least partially formed from stainless steel, such as 316 stainless steel.

Modulator columns of any length and any practical diameter can be used. For example, the modulator columns described herein may have a length ranging from about 0.1 to about 20 cm, such as about 1 to about 15 cm, about 2 to about 10 cm, or about 2 to about 5 cm. Similarly, the modulator columns described herein may have a diameter ranging from about 10 μm to about 2 mm, such as about 30ρ to about 1 mm. Of course, columns with a length that is longer, shorter, or within the aforementioned ranges may be used, and are encompassed by the present disclosure.

The interior of the modulator columns described herein may be coated with any suitable material. In some embodiments, the interior diameter of the modulator columns described herein is coated with a passivating layer of silica, glass, or another non-reactive material. Alternatively or additionally, the interior diameter of the modulator columns of the present disclosure may be coated with thin film of stationary phase, such as a high molecular weight organic material (e.g., a wax or polymer) as a stationary phase.

As discussed previously, differences in the properties of the ground point and a modulator column (or the modulated sections thereof) can give rise to complications such as peak broadening, lack of sensitivity, and other issues. To address these issues, the thermal modulators of the present disclosure may utilize ground points that are thermally matched to adjacent stages of a modulator column.

Thus, in some embodiments of the present disclosure, at least one of the CSA, electrical resistance, specific heat capacity, and thermal mass of the ground points described herein is selected or adjusted to a specific value relative to the value of corresponding properties of adjacent stages of a modulator column. For example, the CSA, electrical resistance, specific heat capacity and thermal mass of the ground points (including combinations thereof) may be the same as corresponding properties of adjacent stages of a modulator column, or may differ from such stages by about −5% to about +5%, such as about −1% to about +1%, or even about −0.5% to about +0.5%, as previously described.

The ground points described herein may be made of any material that is suitable for providing a connection to electrical ground. Non-limiting examples of such materials include metals such as copper, stainless steel (e.g., 316 stainless steel), aluminum, and combinations thereof.

In some embodiments, the ground points and modulator columns described herein are made of the same material. For example, the modulator column and ground points described herein may each be formed from copper, stainless steel (e.g., 316 stainless steel), and aluminum. By forming the modulator column and the ground point from the same material, such components may exhibit many of the same or similar heating properties. For example, by forming a ground point and a modulator column from the same material (e.g., stainless steel), such components may exhibit the electrical resistance, resistivity, $\alpha$, and c. As a result, if the modulator column and ground point are exposed to the same amount of current from a power supply, they may exhibit the same or similar change in temperature in response to heating and cooling forces.

In some instances, however, using the same materials to form a ground point and a modulator column may be insufficient to thermally match the two components. That is, even if a modulator column and a ground point are formed from the same material, the rate at which they change temperature may vary based on a number of factors, such as their thermal mass, area (A) and CSA. Thus, in some embodiments of the present disclosure, the modulator columns (or the modulated stages thereof) and the ground points disclosed herein are formed from the same material, and are structured such that they exhibit the same or substantially the same thermal mass, A (or CSA), as previously described.

Although modulator columns may be custom designed (i.e., their materials and dimensions changed), it may be desirable to utilize one or more commercially available modulator columns in a two stage thermal modulator. Moreover, it may be easier to make adjustments to the design of a ground point than it is to make adjustments to the design of a modulator column. With this in mind, the ground points of the present disclosure may be of any design that is suitable for providing an electrical connection to ground.

Figure 5A:
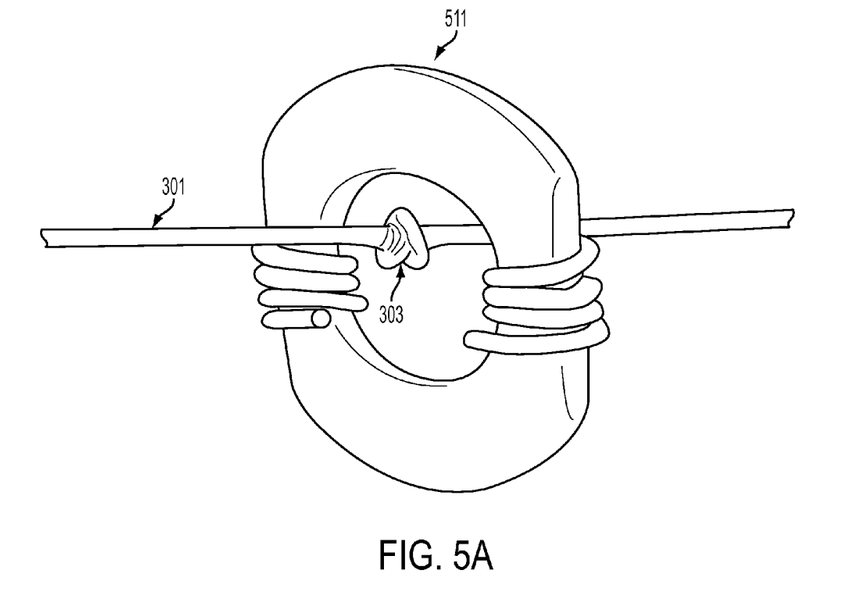
FIG. 5A depicts a non-limiting example of a ground point in accordance with the present disclosure, configured in the form of a knot around a modulator column.

For example, the ground point may take the form of a knotted wire tied around a modulator column. This concept is shown in FIG. 5A, wherein ground point 303 is formed by tying a half hitch knot around modulator column 301. More specifically, ground point 303 may be formed by tying one or more stands of wire around modulator column 301. In some embodiments, the strand or strands forming the ground point have an electrical resistance that is the same as the electrical resistance of modulator column 301, or which differs from the electrical resistance of the modulator column by about 5% or less, about 1% or less, or even about 0.5% or less. Close matching of the electrical resistance of the wire forming ground point 303 and the electrical resistance of modulator column 301 may be achieved by forming ground point 303 out of a wire having the same composition as modulator column 301 (e.g., copper, stainless steel, etc.).

In some embodiments, the wire strands have an area (e.g., a CSA) that is the same as the area of modulator column 301, or which differs from the area of modulator column 301 by about 5% or less, about 1% or less, or even about 0.5% or less. Close matching of the area of modulator column 301 and the area of ground point 303 may be achieved by selecting wire having an appropriate diameter to form ground point 303.

Also shown in FIG. 5A is carrier washer 511. Carrier washer 511 is connected to the ends of the wire forming ground point 303, and couples the ground point to another component of the thermal modulator into which the modulator column and ground point are incorporated, such as the housing 401 shown in FIG. 4. For example, the assembly shown in FIG. 5A may be clamped within housing 401, e.g., by a barrel nut or another fastener. In this way, the barrel nut/fastener can compress on washer 511, completing an electrical connection between modulator column 301, ground point 303, washer 511 and housing 401. Alternatively, the knot may be secured to modulator column 301 and/or housing 401 by another means, such as by laser or e-beam welding.

In one non-limiting embodiment, a ground point is formed by a half hitch knot of stainless steel wire tied around a stainless steel modulator column. This solution is not ideal, however, because the knot around the modulator column has a larger effective area than the column itself, and adds mass to the area being heated. A lower temperature will therefore result at the contact point between the knot and the modulator column. However, the difference in mass can be quite small, meaning that the contact point may get warm enough during heating to transfer all of the analyte in the first stage of the modulator column to the second stage. However, this may require running the two stage thermal modulator at an undesirably high temperature, which could prove problematic in the analysis of thermally labile materials. Thus, while the stainless steel wire may not be a perfect match for the stainless steel of the column (not disclosed by the manufacturer) but the variations in the relevant parameters, $\rho$, $\alpha$, and c, is small enough to not affect the outcome.

Figure 5B:
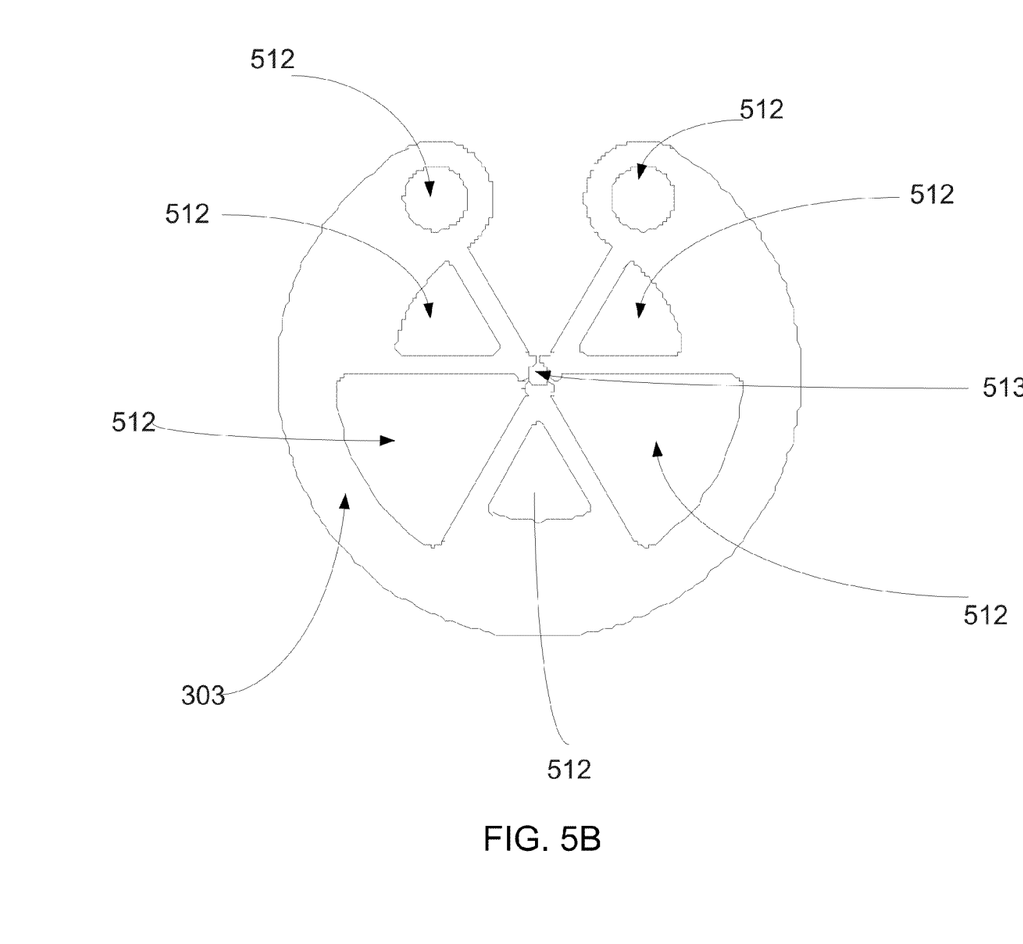
FIG. 5B depicts a non-limiting example a ground point in accordance with the present disclosure, configured in the form of a plate.

The ground points described herein may also take the form of a plate. This concept is shown in FIG. 5B, wherein ground point 303 is generally configured as a plate having holes 512 and a central opening 513. In the non-limiting example shown in FIG. 5B, central opening 513 is sized such that a modulator column may fit through and contact the sides of central opening 513. In this way, ground point 303 can connect the modulator column to electrical ground, either directly or indirectly as previously described. Moreover, ground point 303 may provide support for the modulator column passing through central opening 513.

Figure 6A:
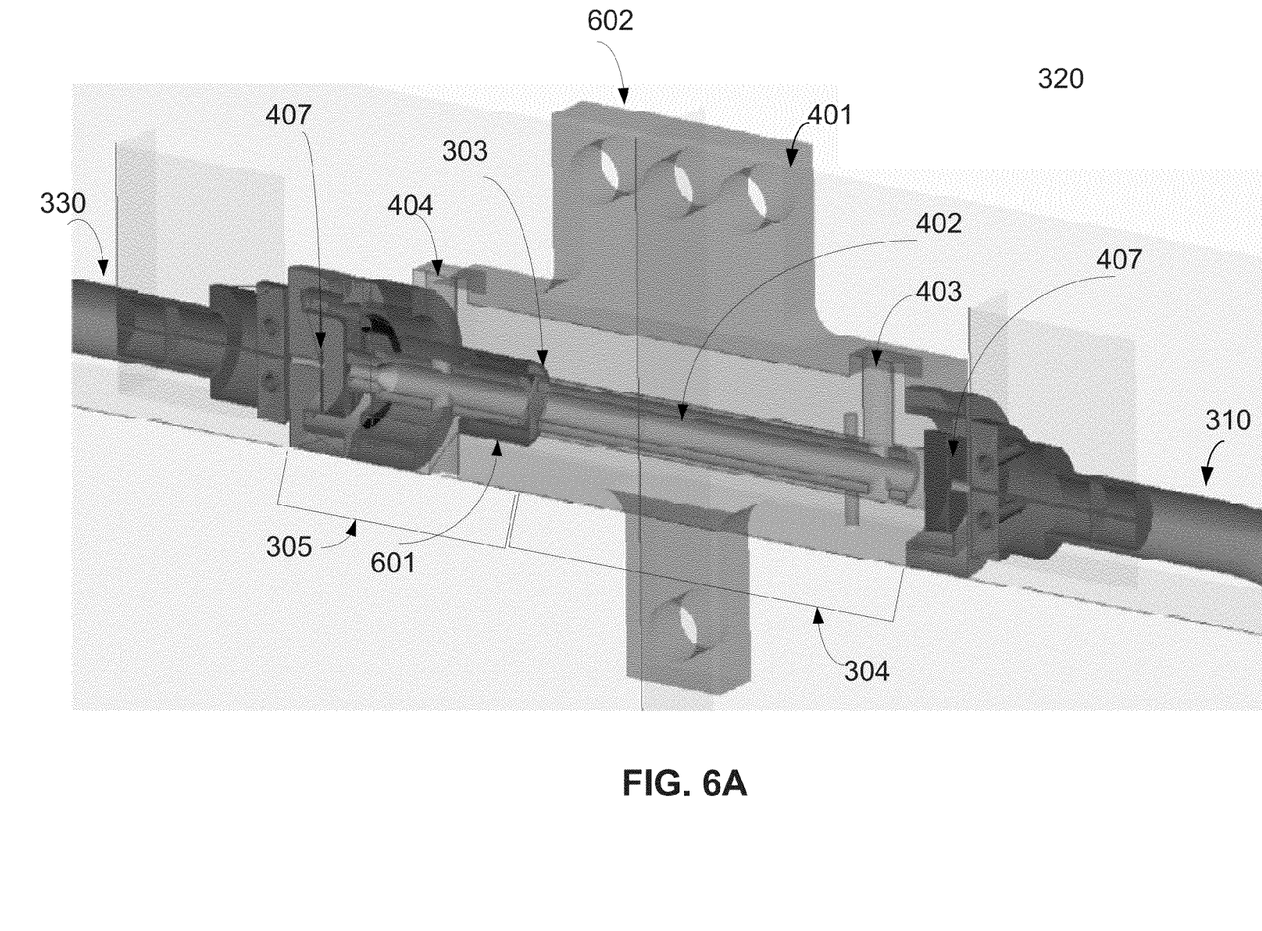
FIG. 6A is cross sectional diagram of a non-limiting example of a multidimensional GC system incorporating a two stage thermal modulator utilizing a ground point plate, in accordance with the present disclosure.
Figure 6B:
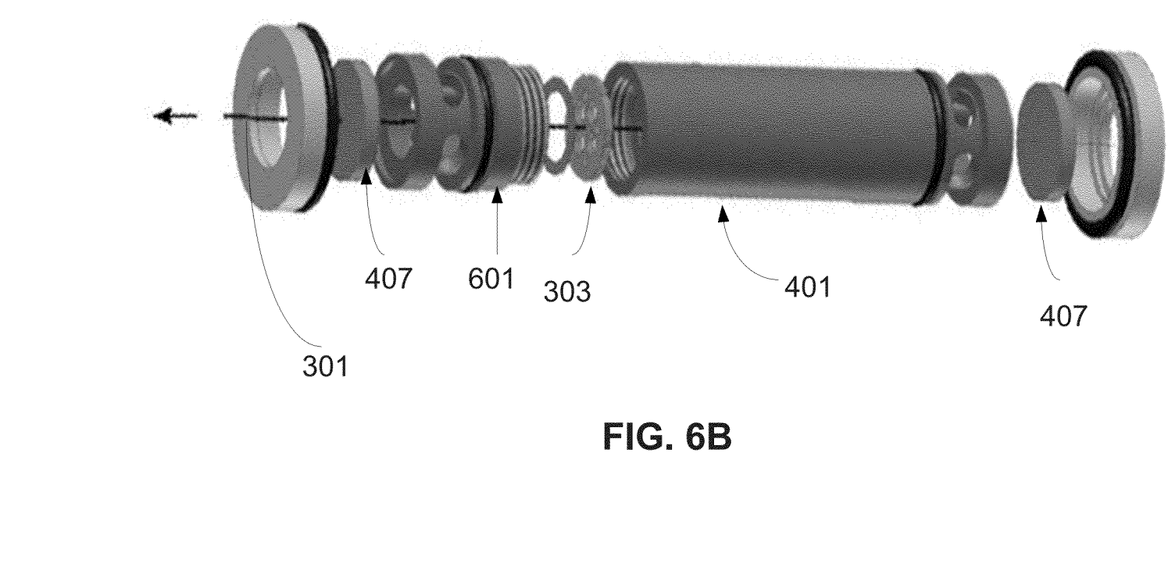
FIG. 6B is an exploded view of a non-limiting example of a two stage thermal modulator including a ground point plate in accordance with the present disclosure.

Like the ground point knot described above, compressive force or another connection means may be used to complete an electrical connection between modulator column 301, ground point 303 and housing 401 of two stage thermal modulator 320. For example, a ground point plate may be coupled to modulator column 301 and housing 401 by way of a barrel nut or other suitable connector, e.g., as shown in FIGS. 6A and 6B (described below). Moreover, a ground point plate such as the one shown in FIG. 5B may be welded, e.g., by e-beam or laser welding, to modulator column 301, housing 401, or both.

As noted above, it may be desirable to adjust the thermal mass of the ground point to approximate the thermal mass of a modulator column, or surrounding stages of a modulator column. In this regard, the thermal mass of a plate ground point, such as the one depicted in FIG. 5B, may be adjusted by machining the plate to a desired thickness, and/or by cutting more or less holes in the plate. This concept is generally illustrated in FIG. 5B, wherein holes 512 are cut into ground point 303. It should be understood, of course, that the particular design shown in FIG. 5B is exemplary only, and that other plate ground point designs may be used in accordance with the present disclosure.

As a non limiting example of two stage thermal modulator utilizing a ground point plate in accordance with the present disclosure, reference is made to FIGS. 6A and 6B. FIG. 6A provides a cross-sectional view of multidimensional GC incorporating a two stage thermal modulator 320 utilizing a ground point plate in accordance with the present disclosure. FIG. 6B provides an exploded view of another non-limiting example of the construction of a two stage thermal modulator column 320 including a ground point plate. Both FIGS. 6A and 6B reference various components of a two-stage thermal modulator that have been previously described in connection with FIGS. 3 and 4, respectively. Accordingly, such components are not specifically described herein with respect to FIGS. 6A and 6B.

As shown in FIGS. 6A and 6B, modulator column 301 is disposed through an opening of ground point 303, which is configured as a plate. Ground point 303 is disposed within cavity 402 of housing 401 of two stage thermal modulator 320, and has a CSA that closely approximates the CSA of the interior of cavity 402. As shown, ground point 303 is coupled to modulator column 301 and housing 401 by way of compression by barrel nut 601. Housing 401 is grounded, e.g., through a separate ground connection or connections at upper portion 602. As a result, ground point 303 provides a pathway to ground for electrical current applied across first stage 304 and second stage 305 by first and second stage power supplies, respectively (power supplies not shown).

As a non-limiting example of a method of operating 2D GC 300, and with reference to FIGS. 3-6B, an analyte sample may be injected into first chromatography column 310. Within first chromatography column 310, components of the analyte sample may be separated into bands based on the affinity of such components to the stationary phase of first chromatography column 310. The separated bands may then be input into modulator column 301.

As noted above, at least a portion of modulator column 301 may be cooled by coolant 302, thereby forming chilled region 306. Modulator column 301 within chilled region 306 is divided into first and second stages 304, 305 by ground point 303. First stage and second stage power supplies 307', 307'' may be independently turned on and off, so as to independently heat stages 303 and 304 of modulator column 301.

Figure 7:
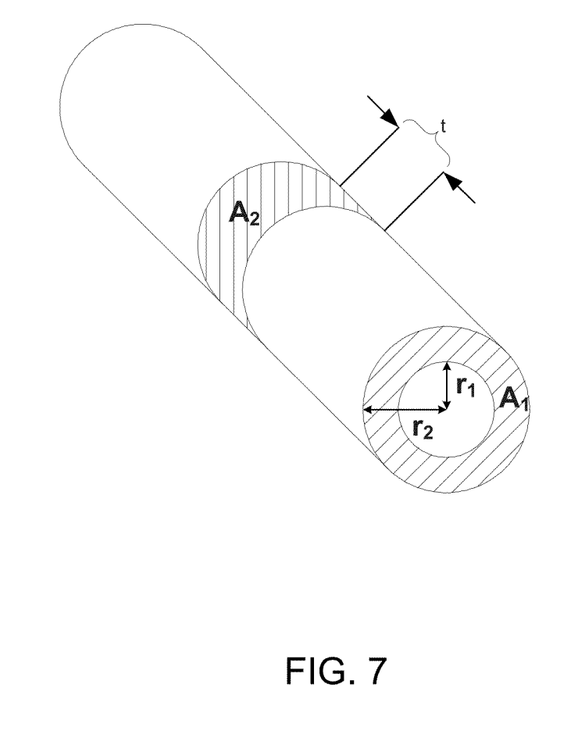
FIG. 7 is a cross sectional view of a modulator column in accordance with a non-limiting embodiment of the present disclosure.

Regardless of whether the ground point is in the form of a knot or a plate, the contact point between the modulator column and the ground point preferably has the same area as the modulator column itself. In instances where the ground point is in the form of a plate, and with reference to FIG. 7, the desired width of the ground point plate may be derived as follows:

$$A_1 = \pi(r_2^2 - r_1^2) \quad (8)$$

$$A_2 = 2\pi r_2 t \quad (9)$$

Where $A_1$ is the cross sectional area of the modulator column, $r_1$ is the inner diameter of the modulator column; $r_2$ is the outer diameter of the modulator column, $A_2$ is the area of the contact point between the modulator column and the ground point, and t is the thickness of the contact patch of the ground point plate. If it is assumed that $A_1 = A_2$, then solving for t yields equation (10) below:

$$t = \pi(r_2^2 - r_1^2)/2\pi r_2. \quad (10)$$

In some embodiments, the contact patch of the ground point plate is around the whole of the circumference of a column. In such instances, a desired thickness of the ground point will correlate to t as derived in equation (10) above. In instances where the contact patch of the ground point is less than the whole circumference of the column, then the thickness of the ground point plate would have to be increased accordingly to account of the lack of contact with certain portions of the column.

Other embodiments of the present disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A two stage thermal modulator, comprising:
   a housing;
   a cavity in said housing, the cavity configured to contain a coolant;
   a modulator column comprising a chilled region disposed within said cavity so as to be in contact with said coolant;
   a ground point coupled to said modulator column and within said chilled region, said ground point operable to connect said modulator column to electrical ground; and
   at least one power supply coupled to said modulator column at a first point and a second point along said modulator column, said at least one power supply operable to resistively heat a first stage of said modulator column and a second stage of said modulator column, said first stage being between said first point and said ground point, said second stage being between said ground point and said second point;
   wherein:
   said modulator column has a resistivity R1, a thermal mass TM1, and a cross sectional area CSA1;
   said ground point has a resistivity R2, a thermal mass TM2, and a cross sectional area CSA2; and
   at least two of the following relationships are true:
   R2 differs from R1 by less than or equal to about 5%;
   TM2 differs from TM1 by less than or equal to about 5%; and
   CSA1 differs from CSA2 by less than or equal to about 5%.

2. The two stage thermal modulator of claim 1, wherein all of the following relationships are true:
   R2 differs from R1 by less than or equal to about 5%;
   TM2 differs from TM1 by less than or equal to about 5%; and
   CSA1 differs from CSA 2 by less than or equal to about 5%.

3. The two stage thermal modulator of claim 2, wherein said ground point comprises at least one of a knot and a plate.

4. The two stage thermal modulator of claim 1, wherein at least one of the following relationships is true:
   R2 differs from R1 by less than or equal to about 1%;
   TM2 differs from TM1 by less than or equal to about 1%; and
   CSA1 differs from CSA2 by less than or equal to about 1%.

5. The two stage thermal modulator of claim 1, wherein at least two of the following relationships are true:
   R2 differs from R1 by less than or equal to about 1%;
   TM2 differs from TM1 by less than or equal to about 1%; and
   CSA1 differs from CSA2 by less than or equal to about 1%.

6. The two stage thermal modulator of claim 1, wherein all of the following relationships are true:
   R2 differs from R1 by less than or equal to about 1%;
   TM2 differs from TM1 by less than or equal to about 1%; and
   CSA1 differs from CSA2 by less than or equal to about 1%.

7. The two stage thermal modulator of claim 1, wherein at least one of the following relationships is true:
   R2=R1;
   TM2=TM1; and
   CSA1=CSA2.

8. The two stage thermal modulator of claim 1, wherein at least two of the following relationships are true:
R2=R1;
TM2=TM1; and
CSA1=CSA2.

9. The two stage thermal modulator of claim 1, wherein all of the following relationships are true:
R2=R1;
TM2=TM1; and
CSA1=CSA2.

10. The two stage thermal modulator of claim 1, wherein said modulator column and said grounding point are made of the same material.

11. The two stage thermal modulator of claim 1, wherein said ground point comprises at least one of a knot and a plate.

12. A method for temperature modulation in gas chromatography comprising:
introducing a sample into a modulator column of a two stage thermal modulator, the modulator column comprising a chilled region disposed within a cavity of a housing so as to thermally contact a coolant disposed within said cavity;
wherein said two stage thermal modulator comprises:
a ground point coupled to said modulator column and within said chilled region, said ground point operable to connect said modulator column to electrical ground;
a power supply electrically coupled to said modulator column at a first point and a second point along said modulator column, said power supply operable to resistively heat a first stage of said modulator column and a second stage of said modulator column, said first stage being between said first point and said ground point, said second stage being between said ground point and said second point;
and wherein:
said modulator column has a resistivity R1, a thermal mass TM1, and a cross sectional area CSA1;
said ground point has a resistivity R2, a thermal mass TM2, and a cross sectional area CSA2;
and at least two of the following relationships are true:
R2 differs from R1 by less than or equal to about 5%;
TM2 differs from TM1 by less than or equal to about 5%; and
CSA1 differs from CSA2 by less than or equal to about 5%.

13. The method of claim 12, wherein all of the following relationships are true:
R2 differs from R1 by less than or equal to about 5%;
TM2 differs from TM1 by less than or equal to about 5%; and
CSA1 differs from CSA2 by less than or equal to about 5%.

14. The method of claim 13, wherein said ground point comprises at least one of a knot and a plate.

15. The method of claim 12, wherein at least one of the following relationships is true:
R2 differs from R1 by less than or equal to about 1%;
TM2 differs from TM1 by less than or equal to about 1%; and
CSA1 differs from CSA2 by less than or equal to about 1%.

16. The method of claim 12, wherein at least two of the following relationships are true:
R2 differs from R1 by less than or equal to about 1%;
TM2 differs from TM1 by less than or equal to about 1%; and
CSA1 differs from CSA2 by less than or equal to about 1%.

17. The method of claim 12, wherein all the following relationships are true:
R2 differs from R1 by less than or equal to about 1%;
TM2 differs from TM1 by less than or equal to about 1%; and
CSA1 differs from CSA2 by less than or equal to about 1%.

18. The method of claim 12, wherein at least one of the following relationships is true:
R2=R1;
TM2=TM1; and
CSA1=CSA2.

19. The method of claim 12, wherein at least two of the following relationships are true:
R2=R1;
TM2=TM1; and
CSA1=CSA2.

20. The method of claim 12, wherein all of the following relationships are true:
R2=R1;
TM2=TM1; and
CSA1=CSA2.

21. The method of claim 12, wherein said modulator column and said ground point are made of the same material.

22. The method of claim 12, wherein said ground point comprises at least one of a knot and a plate.

23. A modulator column for use in a two stage thermal modulator, the modulator column comprising a ground point, a first stage proximal to the ground point, and a second stage distal to the ground point, wherein:
said modulator column has a resistivity R1, a thermal mass TM1, and a cross sectional area CSA1;
said ground point has a resistivity R2, a thermal mass TM2, and a cross sectional area CSA2:
at least two of the following relationships are true:
R2 differs from R1 by less than or equal to about 5%;
TM2 differs from TM1 by less than or equal to about 5%; and
CSA1 differs from CSA2 by less than or equal to about 5%; and
when an electric current is passed through the first stage and the grounding point or the second stage and the grounding point, the ground point exhibits a temperature that is less than about 5% different from the temperature of the first stage or the second stage, respectively.

* * * * *